(12) United States Patent
Cetingul et al.

(10) Patent No.: US 9,918,639 B2
(45) Date of Patent: Mar. 20, 2018

(54) MAGNETIC RESONANCE IMAGING WITH ASYMMETRIC RADIAL SAMPLING AND COMPRESSED-SENSING RECONSTRUCTION

(71) Applicant: Siemens Healthcare GmbH, Erlangen (DE)

(72) Inventors: Hasan Ertan Cetingul, Baltimore, MD (US); Mariappan S. Nadar, Plainsboro, NJ (US); Peter Speier, Erlangen (DE); Michaela Schmidt, Uttenreuth (DE)

(73) Assignee: Siemens Healthcard GmbH, Erlangen (DE)

( * ) Notice: Subject to any disclaimer, the term of this patent is extended or adjusted under 35 U.S.C. 154(b) by 694 days.

(21) Appl. No.: 14/531,676

(22) Filed: Nov. 3, 2014

(65) Prior Publication Data

US 2015/0126850 A1 May 7, 2015

Related U.S. Application Data

(60) Provisional application No. 61/901,081, filed on Nov. 7, 2013.

(51) Int. Cl.
*A61B 5/00* (2006.01)
*A61B 5/0402* (2006.01)
*A61B 5/04* (2006.01)
*A61B 5/0452* (2006.01)
(Continued)

(52) U.S. Cl.
CPC ............ *A61B 5/0044* (2013.01); *A61B 5/004* (2013.01); *A61B 5/04* (2013.01); *A61B 5/0402* (2013.01);
(Continued)

(58) Field of Classification Search
CPC ......... A61B 5/0044; A61B 5/055; A61B 5/05; A61B 5/0452; A61B 5/04; A61B 5/004; A61B 5/7289; A61B 5/0402; G01R 33/56325; G01R 33/4824; G01R 33/561; G01R 33/546; G01R 33/4818; G01R 33/48; G01R 33/20; G01R 33/56; G01R 33/56308
See application file for complete search history.

(56) References Cited

U.S. PATENT DOCUMENTS 7,592,808 B1 * 9/2009 King ................ G01R 33/56545
324/307
8,089,278 B1 * 1/2012 Du ..................... G01R 33/4824
324/307
(Continued)

OTHER PUBLICATIONS

H. Bauschke and J. Borwein, SIAM Review, 38(3):367-426, 1996.
(Continued)

*Primary Examiner* — Peter Luong (57) ABSTRACT

A method for acquiring cine images using a magnetic resonance imaging (MRI) system includes selecting an asymmetric radial sampling scheme providing an asymmetric view of k-space corresponding to a desired image resolution. Radial k-space data is acquired using the asymmetric radial sampling scheme, wherein slice-orientation of the radial k-space data is continuously modified while acquiring the radial k-space data. A plurality of cine images are reconstructed from the radial k-space data using a compressed-sensing method.

16 Claims, 6 Drawing Sheets

(51) Int. Cl.
*A61B 5/05* (2006.01)
*A61B 5/055* (2006.01)
*G01R 33/20* (2006.01)
*G01R 33/48* (2006.01)
*G01R 33/563* (2006.01)
*G01R 33/56* (2006.01)
*G01R 33/54* (2006.01)
*G01R 33/561* (2006.01)

(52) U.S. Cl.
CPC .............. *A61B 5/0452* (2013.01); *A61B 5/05* (2013.01); *A61B 5/055* (2013.01); *A61B 5/7289* (2013.01); *G01R 33/20* (2013.01); *G01R 33/48* (2013.01); *G01R 33/4818* (2013.01); *G01R 33/4824* (2013.01); *G01R 33/56* (2013.01); *G01R 33/563* (2013.01); *G01R 33/56308* (2013.01); *G01R 33/56325* (2013.01); *G01R 33/546* (2013.01); *G01R 33/561* (2013.01)

(56) References Cited

U.S. PATENT DOCUMENTS

| | | | |
|---|---|---|---|
| 2009/0143666 A1* | 6/2009 | Edelman | A61B 5/055 600/410 |
| 2009/0275822 A1* | 11/2009 | Detsky | A61B 5/055 600/413 |
| 2015/0091563 A1* | 4/2015 | Lu | A61B 5/055 324/309 |

OTHER PUBLICATIONS

M. Lustig et al., Mag Reson Med, 6:1182-1195, 2007.
L. Feng et al., Proc Intl Soc Mag Reson Med, #1117, 2012.
J. Liu et al., Proc Intl Soc Mag Reson Med, #4249, 2012.
J. Liu et al., technical report, 2012.
J.A. Fessler et al., IEEE T Signal Process, 51:560-574, 2003.
A. Beck and M. Teboulle, SIAM J Imag Sci, 2:183-202, 2009.

* cited by examiner

MAGNETIC RESONANCE IMAGING WITH ASYMMETRIC RADIAL SAMPLING AND COMPRESSED-SENSING RECONSTRUCTION

CROSS-REFERENCE TO RELATED APPLICATIONS

This application claims priority to U.S. provisional application Ser. No. 61/901,081 filed Nov. 7, 2013 which is incorporated herein by reference in its entirety.

TECHNOLOGY FIELD

The present invention relates generally to methods, systems, and apparatuses for Magnetic Resonance Imaging (MRI) utilizing asymmetric radial sampling schemes and compress-sensing reconstruction techniques. The disclosed methods, systems, and apparatuses may be applied, for example, to fast free-breathing cardiac cine MRI applications.

BACKGROUND

Two-dimensional (2D) segmented cardiac cine Magnetic Resonance Imaging (MRI) is a time-resolved imaging technology that is routinely used for non-invasive assessment of the cardiac function. This technology requires breath-holds and a regular heartbeat from the individual being imaged. In situations where this is not possible, 2D unsegmented real-time Balanced Steady-State Free Precession (bSSFP) cine MRI, accelerated by parallel imaging and partial Fourier techniques, is often used with reduced quality. bSSFP requires short inter-pulse distance repetition time (TR) for robustness against BO field inhomogeneities and flow. In Cartesian bSSFP, the TR is reduced by partial Fourier acquisition in the readout direction (i.e., the early part of the echo is omitted and the readout is thus shortened). Reconstruction can use zero-filling or data generating algorithms like projection onto convex sets (POCS). The reduction in TR can be either used to increase the frame rate, or to increase the number of views per frame.

Recently, the idea of exploiting the compressibility of MR images in a transform domain has resulted in the development of compressed-sensing (CS) based MRI reconstruction techniques which can accelerate acquisition times in cardiac cine by enabling image reconstruction from highly under-sampled k-space data. Some conventional imaging systems combine CS-type reconstruction techniques with radial sampling strategies to further reduce the overall time required to acquire and process images. These systems typically utilize views which are placed symmetrically around the k-space center to form full echoes for acquisition. However, the symmetric placement of views introduces a redundancy because it ignores the complex conjugate symmetry that exists between signals from the outer parts of the k-space connected by point symmetry. Accordingly, it is desired to provide techniques which exploit the complex conjugate symmetry that exists in k-space to further accelerate acquisition time.

SUMMARY

Embodiments of the present invention address and overcome one or more of the above shortcomings and drawbacks, by providing methods, systems, and apparatuses related to the use of interleaved-angle radial sampling with asymmetric echoes, instead of the conventional full echoes, for robust fast free-breathing cardiac cine MRI. The proposed schemes may lead to a reduction in repetition-time (and hence a reduction in total data acquisition time) without a severe degradation in reconstruction.

According to some embodiments of the present invention, a method for acquiring cine images using a magnetic resonance imaging (MRI) system includes selecting an asymmetric radial sampling scheme providing an asymmetric view of k-space corresponding to a desired image resolution. Radial k-space data is acquired using the asymmetric radial sampling scheme, wherein slice-orientation of the radial k-space data is continuously modified while acquiring the radial k-space data. A plurality of cine images are reconstructed from the radial k-space data using a compressed-sensing method.

In some embodiments of the aforementioned method, the asymmetric radial sampling scheme is an interleaved-angle asymmetric radial sampling scheme. The interleaved-angle asymmetric radial sampling scheme may be implemented various ways. For example, in one embodiment the interleaved-angle asymmetric radial sampling scheme includes a full-echo sampling scheme portion to be applied in a center region of k-space; and a secondary sampling scheme portion to be applied in a remaining area of k-space which excludes the center region of k-space. Additionally, the type of the interleaved-angle asymmetric radial sampling scheme may vary. For example, weak, strong, or half-echo interleaved-angle asymmetric radial sampling schemes may be used in different embodiments of the present invention. In some embodiments, the interleaved-angle asymmetric radial sampling scheme distributes the asymmetric view of k-space over $2\pi$.

The implementation details of the compressed-sensing method may also vary according to different embodiments of the present invention. For example, in one embodiment, a density compensation value corresponding to the asymmetric view of k-space is determined as part of the method. The compressed-sensing method may apply this density compensation value during the reconstruction of the plurality of cine images. In some embodiments, the density compensation value corresponds to a number of samples to be acquired in the asymmetric view of k-space. In one embodiment, the compressed-sensing method incorporates an estimated coil sensitivity map generated in parallel with the reconstruction. In some embodiments, the compressed-sensing method enforces $L_2$-type data consistency and a $L_1$-type non-smooth penalty with respect to the radial k-space data.

According to other embodiments of the present invention, a second method for acquiring cine images using a MRI system includes selecting an interleaved-angle asymmetric radial sampling scheme providing an asymmetric view of k-space corresponding to a desired image resolution. Radial k-space data is acquired over a number of interleaves using the interleaved-angle asymmetric radial sampling scheme. In one embodiment, the radial k-space data is acquired using a Balanced Steady-State Free Precession (bSSFP) sequence. The radial k-space data is segmented into a plurality of overlapping temporal windows based on the number of interleaves. A plurality of cine images is reconstructed iteratively from the overlapping temporal windows using a compressed-sensing method.

Various enhancements, modifications, and/or additional features may be added to the aforementioned second method for acquiring cine images. For example, in some embodiments, this compressed-sensing method determines a density compensation value corresponding to the asymmetric view of k-space and applies the density compensation value during the reconstruction of the plurality of cine images. The density compensation value may correspond to, for example, a number of samples to be acquired in the asymmetric view of k-space. In some embodiments, the compressed-sensing method incorporates an estimated coil sensitivity map that may or may not be generated in parallel with the reconstruction. In one embodiment, the compressed-sensing method enforces $L_2$-type data consistency and a $L_1$-type non-smooth penalty with respect to the radial k-space data.

According to other embodiments of the present invention, a system for acquiring cine images using a MRI system includes an operator interface, a plurality of radio frequency, an a central control computer. The operator interface is configured to select an asymmetric radial sampling scheme providing an asymmetric view of k-space corresponding to a desired image resolution. The plurality of radio frequency coils is configured to acquire radial k-space data using the asymmetric radial sampling scheme. In one embodiment, slice-orientation of the radial k-space data is continuously modified while acquiring the radial k-space data. The central control computer unit is configured to reconstruct a plurality of cine images from the radial k-space data using a compressed-sensing method. In some embodiments, the system also includes an ECG acquisition system configured to acquire a cardiac timing signal. In these embodiments, the central control computer unit is further configured to divide the radial k-space data in overlapping temporal windows based on the cardiac timing signal and reconstruction of the plurality of cine images is based on these overlapping temporal windows.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at methods, systems, and apparatuses for fast free-breathing cardiac Magnetic Resonance Imaging (MRI). More specifically, in some embodiments, the techniques described herein combine a Balanced Steady-State Free Precession (bSSFP) for interleaved-angle radial sampling schemes with echoes at different levels of asymmetry and a compressed-sensing (CS) reconstruction method tuned for radial k-space data. However, it should be noted that the present invention is not limited to bSSFP and interleaved sampling. For example, in other embodiments, the techniques described herein may be applied to other types of MRI sequences including, without limitation, gradient-recalled echo (GRE) and Turbo Spin Echo (TSE) pulse sequences. Additionally, in some embodiments, alternatives to interleaved sampling are applied such as, for example, sampling schemes that produce complementary patterns over successive images, so that averaging over successive images generate complete k-space coverage (e.g., golden angle sampling).

The disclosed methods, systems, and apparatuses may be applied, for example, to fast free-breathing cardiac cine MRI applications. Radial sampling patterns are particularly well suited for cine MRI because their frequent acquisition of the k-space center region (1) reduces sensitivity to motion and improves visualization of dynamics, and in a CS-type reconstruction, (2) allows exploitation of sparsity along both image dimensions. In conventional radial imaging, the views are placed symmetrically around the k-space center, forming full echoes for acquisition. Yet, since the phase maps are typically smooth, the signals from the outer parts of the k-space connected by point symmetry have complex conjugate symmetry. An asymmetric echo benefits from this redundancy and omits (samples from) the outer part of one side of the view without subsequent data generation.

Figure 1:
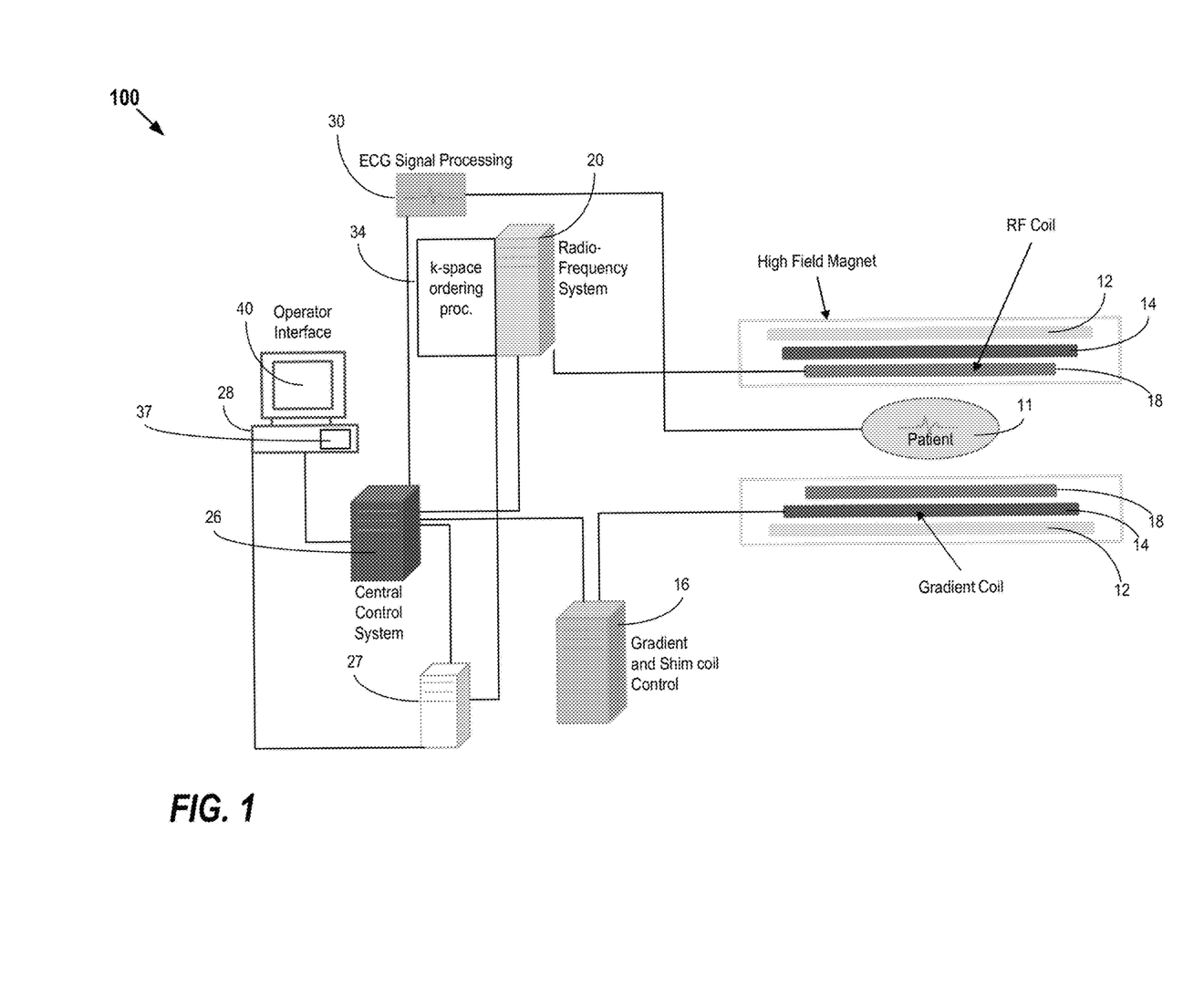
FIG. 1 shows a system for ordering acquisition of frequency domain components representing MR image data for storage in a k-space storage array, as used by some embodiments of the present invention.

FIG. 1 shows a system 100 for ordering acquisition of frequency domain components representing MR image data for storage in a k-space storage array, as used by some embodiments of the present invention. In system 100, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MR imaging device magnetic field resulting from patient anatomical variation and other sources. The magnetic field gradients include a slice-selection gradient magnetic field, a phase-encoding gradient magnetic field and a readout gradient magnetic field that are applied to patient 11.

Further RF (radio frequency) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11. For example, as described in greater detail below, in some embodiments, the central control unit 26 directs the various components of the system 100 to acquire radial k-space data using a bSSFP sequence with an interleaved-angle asymmetric radial sampling scheme.

In response to applied RF pulse signals, the RF coil 18 receives MR signals, i.e., signals from the excited protons within the body as they return to an equilibrium position established by the static and gradient magnetic fields. The MR signals are detected and processed by a detector within RF module 20 and k-space component processor unit 34 to provide an MR dataset to an image data processor for processing into an image. In some embodiments, the image data processor is located in central control unit 26. However, in other embodiments such as the one depicted in FIG. 1, the image data processor is located in a separate unit 27. ECG synchronization signal generator 30 provides ECG signals used for pulse sequence and imaging synchronization. A two or three dimensional k-space storage array of individual data elements in k-space component processor unit 34 stores corresponding individual frequency components comprising an MR dataset. The k-space array of individual data elements has a designated center and individual data elements individually have a radius to the designated center;

A magnetic field generator (comprising coils 12, 14 and 18) generates a magnetic field for use in acquiring multiple individual frequency components corresponding to individual data elements in the storage array. The individual frequency components are successively acquired in an order in which radius of respective corresponding individual data elements increases and decreases along a substantially spiral path as the multiple individual frequency components is sequentially acquired during acquisition of an MR dataset representing an MR image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components is substantially minimized.

Central control unit 26 uses information stored in an internal database to process the detected MR signals in a coordinated manner to generate high quality images of a selected slice(s) of the body (e.g., using the image data processor) and adjusts other parameters of system 100. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control unit 26 and enables user modification of magnetic resonance imaging signals in substantially real time. Display processor 37 processes the magnetic resonance signals to provide image representative data for display on display 40, for example.

The system 100 described in FIG. 1 may be used to implement a framework for fast free-breathing cardiac cine MRI. More specifically, using the techniques described herein, a subject may be imaged using a fluoroscopic bSSFP sequence utilizing interleaved-angle radial sampling schemes with echoes at different levels of asymmetry. The acquired k-space data may then be processed using a compress-sensing reconstruction method tuned for radial k-space data.

Figure 2:
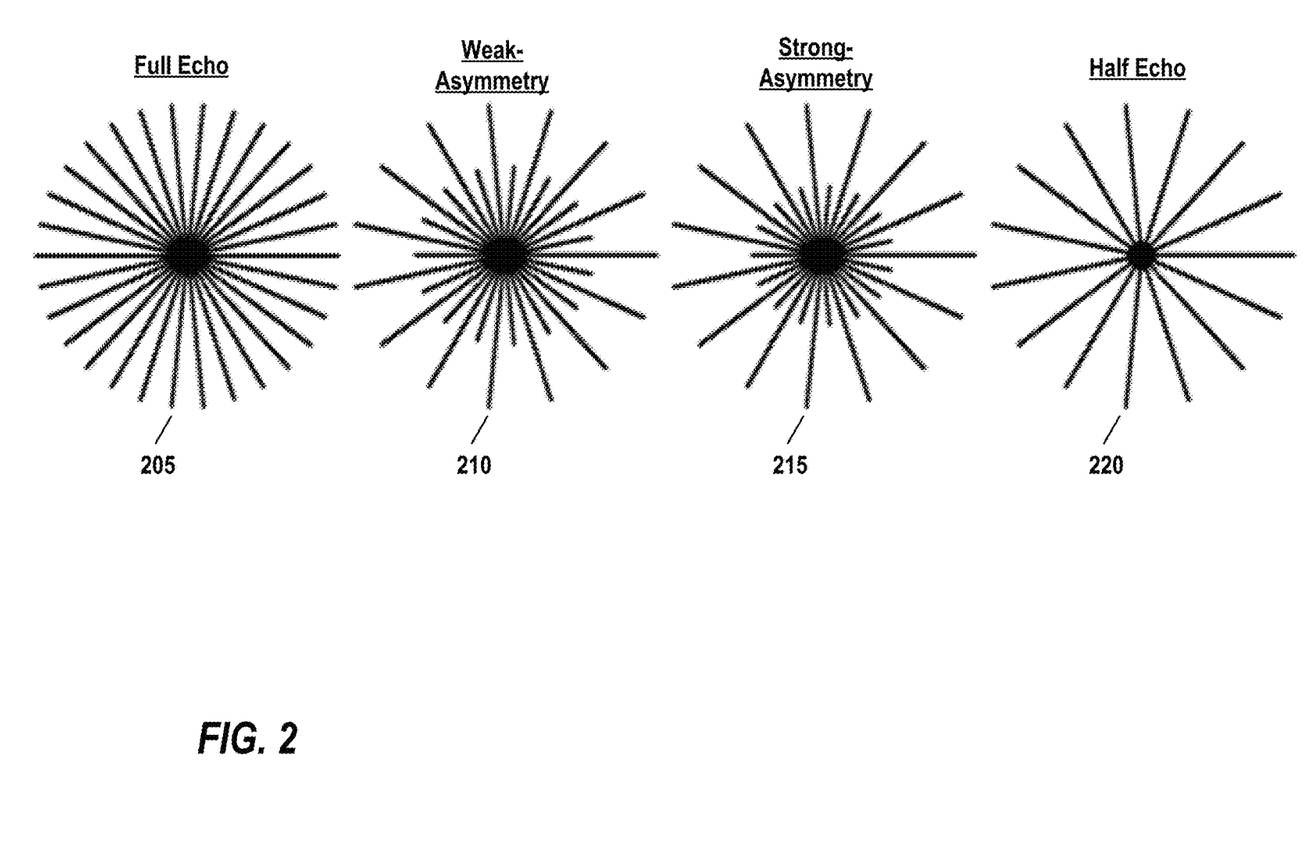
FIG. 2 provides examples of inter-leaved angle radial sampling with views at different levels of symmetry, according to some embodiments of the present invention.

FIG. 2 provides examples of inter-leaved angle radial sampling with views at different levels of symmetry, according to some embodiments of the present invention. More specifically, these images 205, 210, 215, and 220 illustrate the application a modified fluoroscopic bSSFP sequence for interleaved-angle radial sampling schemes with echoes at different levels of asymmetry. In FIG. 2, the images 205, 210, 215, and 220 show the radial sampling schemes for full-echo (FE), weak asymmetry (WA), strong asymmetry (SA), and half-echo (HE), respectively.

The sampling schemes in images 205, 210, 215, and 220 correspond to 192+192 samples, 112+192 samples, 88+192 samples, and 16+192 samples, respectively. Note that the number of samples is inversely proportional to the level of asymmetry. The views are distribute over $2\pi$ (instead of $\pi$) to make the sampling pattern approximately symmetric. Thus, the density compensation D (applied to reduce radial streaks) is a function of the radius r (and not of the azimuth $\varphi$), but a piecewise function of the form $D(r) \sim \{1/r$ for $r<R$; $0.5/r$ for $r \geq R\}$, where R is the number of samples on the asymmetric side of the view (e.g., R=88 for SA in image 215 and R=16 for HE in image 220). Various techniques may be used for calculating the coil sensitivity maps (CSMs). For example, in one embodiment, the CSMs are calculated using based on a 24×24 central k-space region, making CSMs independent of the level of asymmetry up to a certain point.

Figure 3:
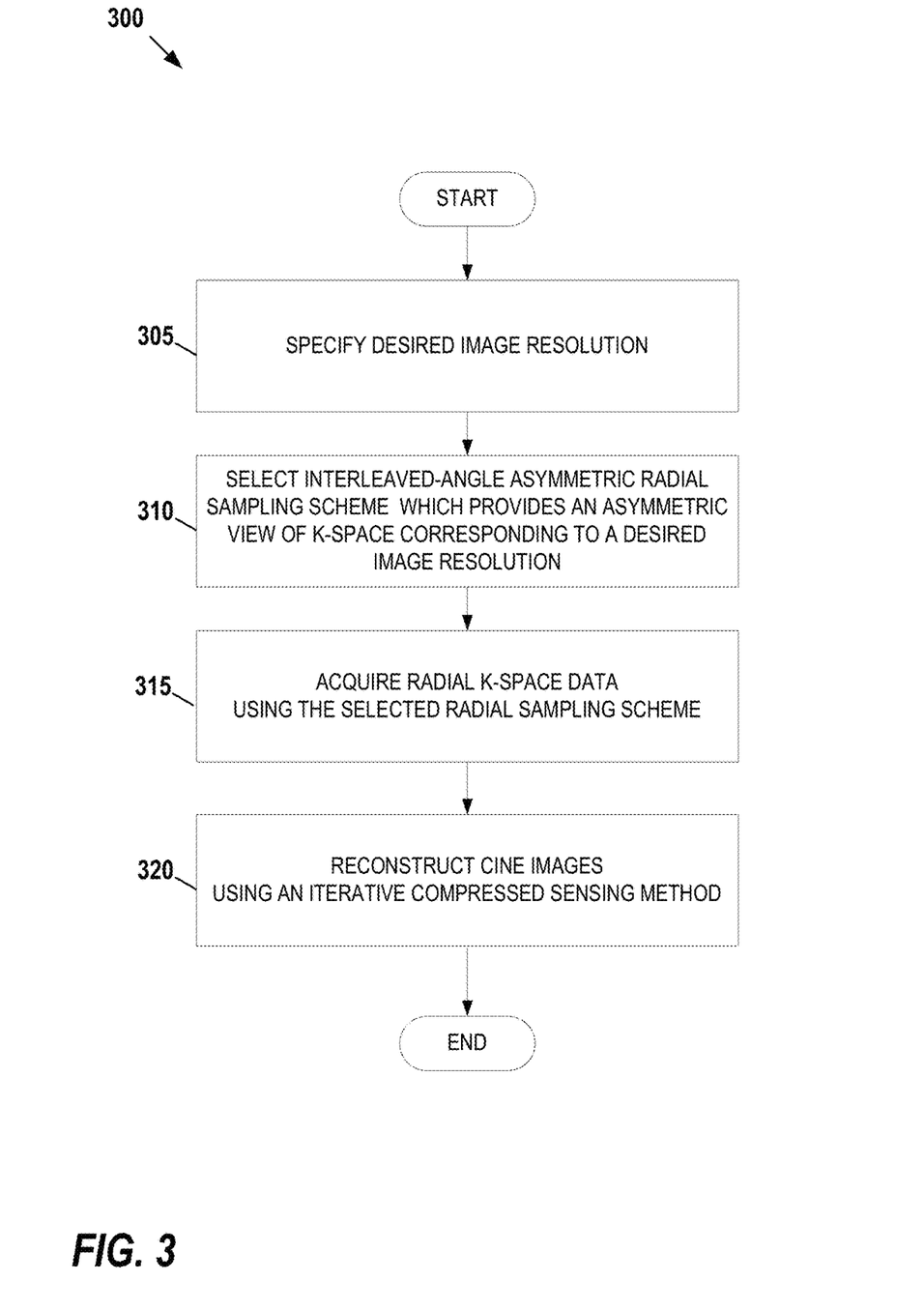
FIG. 3 illustrates a method for acquiring cine images using an MRI system, according to some embodiments of the present invention.

FIG. 3 illustrates a method 300 for acquiring cine images using an MRI system, according to some embodiments of the present invention. At 305, a desired image resolution is specified either explicitly (e.g., based on operator input) or implicitly (e.g., based on pre-defined settings associated with the MRI system or the area of interest to be imaged). Then, at 310, an interleaved-angle asymmetric radial sampling scheme is selected which provides an asymmetric view of k-space corresponding to a desired image resolution.

Various asymmetric radial schemes may be used in the scope of the present invention. In various embodiments, depending on the desired asymmetry, a full-echo sampling scheme, a weak asymmetry sampling scheme, a strong asymmetry sampling scheme, or a half-echo sampling scheme may be used. In other embodiments, different interleaved-angle radial asymmetric sampling schemes may be used. For example, these schemes may utilize different levels of asymmetry given by the ratio of the number of samples measured on the asymmetric side of the view to the number of samples on the symmetric (or complete) side of the view as well as multiple coils during the acquisition.

The exact radial sampling scheme selected at 310 depending on the anticipated characteristics of the image data. For example, if there will be little or no phase variation in image, then a half-echo sampling scheme may be employed. If the image will be complex with phase variation, then (in principle) a full-echo scheme should be used. However, if phase variations are low in frequency, a sampling scheme may be used which only measures full-echo around the center of k-space (i.e., only measuring in symmetric fashion where there is a phase variation. For example, in one embodiment, the asymmetric radial schemes selected at 310 may include a full-echo sampling scheme portion to be applied in a center region of k-space a secondary sampling scheme portion (e.g., employing half-echo) to be applied in the remaining area of k-space.

Continuing with reference to FIG. 3, at 315, the MRI system acquires radial k-space data using the interleaved-angle asymmetric radial sampling scheme. In some embodiments, a conventional pulse sequence such as bSSFP is tailored to implement the sampling scheme. In some embodiments, the scheme is desired to continuously modify the slice-orientation of the radial k-space data (e.g., via modification of the applied gradients) while the data is acquired.

The measurement made at 315 may be modified by tuned one or more acquisition parameters. For example, in some embodiments, acquisition is tuned to maximize image frame rate while maintaining sufficient image quality, and minimize total acquisition to prevent slice shift and rotation from introducing strong inconsistencies in the data. In one embodiment, acquisition is also tuned for a small enough temporal footprint to freeze motion (i.e., real-time/unsegmented/fluoroscopic), which need not be constrained by the patient holding his/her breath. In some embodiments, data may be acquired as a stack of short axis 2D slices. In some embodiments, data may be acquired as a set of long axis 2D slices with different rotation angles around the long axis of the heart. Moreover, in some embodiments, both short axis stacks and long axis sweeps are acquired.

Returning to FIG. 3, at 320, a plurality of cine images are reconstructed from the radial k-space data using a compressed-sensing (CS) method. In some embodiments, the CS method enforces $L_2$-type data consistency and $L_1$-type non-smooth penalty (or regularization). Various CS-type iterative image reconstruction techniques may be applied with different data consistency and/or regularization/penalty terms, according to different embodiments of the present invention. In some embodiments, the complete dynamic reconstruction may be performed considering an overlapping sliding window of length T in time, where T was set to an integer multiple of the number of interleaves. Timing may be based, for example, on data from external components such as ECG acquisition system or a respiratory phase measurement system.

For example, in some embodiments, the reconstruction performed at 320 is based on a CS-type MR reconstruction method which applies an $L_1$ regularization based on the redundant Haar wavelets. Under a parallel imaging scheme with $N_C$ receiver coils, the problem is of the form:

$$\min_x \tfrac{1}{2}\Sigma_{t=1}^{T}\Sigma_{c=1}^{Nc}\|y_t^c - \Phi_t(s^c \odot x_t)\|_2^2 + \|\lambda^{3D} \odot (W^{3D}x)\|_1. \qquad (1)$$

In the first (i.e., data fidelity) term, $x_t$ is the 2D image at time t, $s^c$ is the coil sensitivity map (CSM) for coil c and, $s^c \odot x_t$ is the coil image of coil c at time t (with $\odot$ denoting the component-wise product of two matrices). $\Phi_t$ represents the acquisition operator and $y_t^c$ is the acquired k-space data by coil c at time t. In the second (i.e., non-smooth penalty) term, x is the concatenation of $\{x_t\}_{t=1}^{T}$ into a 3D tensor, $W^{3D}$ is the weighted 3D redundant Haar wavelets, and $\lambda^{3D}$ is the tensor of weights applied on the wavelet coefficients of x. In optimizing (1), the operator $\Phi_t$ may be implemented using Fessler's NUFFT with density compensation D(r) applied on the k-space data and the problem may be solved using a Nesterov type solver. For example, in some embodiments, conventional solvers such as Fast Iterative Shrinkage-Thresholding Algorithm (FISTA) or Alternating Direction Method of Multipliers (ADMM) may be used. In other embodiments, custom solvers (e.g., modifications of conventional solvers) may be used.

In some embodiments, the method 300 may include an additional step (not shown in FIG. 3) where a density compensation value corresponding to the number of samples in the asymmetric view of k-space is determined. Then, at 320 this density compensation value may be used to tune reconstruction in order to reduce radial streaks in the resultant images.

The proposed framework discussed herein was evaluated on phantom and real data (from a healthy volunteer) acquired on a 1.5T clinical MR scanner (MAGNETOM Aera, Siemens AG Healthcare, Erlangen, Germany). Dynamics in the phantom were generated by shifting the slice position by 0.1 mm along the slice normal between frames. The k-space data for the phantom was measured using different radial trajectories, i.e., 15 views per frame with asymmetries given in FIG. 2, with 23 interleaves, 30 coils, and FOV=250 mm×250 mm. A series of 100 images of size 192×192 was reconstructed. The volunteer cardiac data was acquired with asymmetries full echo and strongly-asymmetric using a protocol with 15 views, 20 interleaves, and 32 coils (slice thickness=7 mm, FOV=250 mm×250 mm) to reconstruct a series of 3700 short-axis images of size 192×192. The table below shows the asymmetries and RF spacing (as TR) for these two datasets:

| Data Type | Asymmetry (%) | TR (ms) |
| --- | --- | --- |
| Phantom (fe/wa/sa/he) | 0/42/54/92 | 3.45/3.09/2.98/2.66 |
| Clinical (fe/sa) | 0/54 | 2.80/2.45 |

Figure 4A:
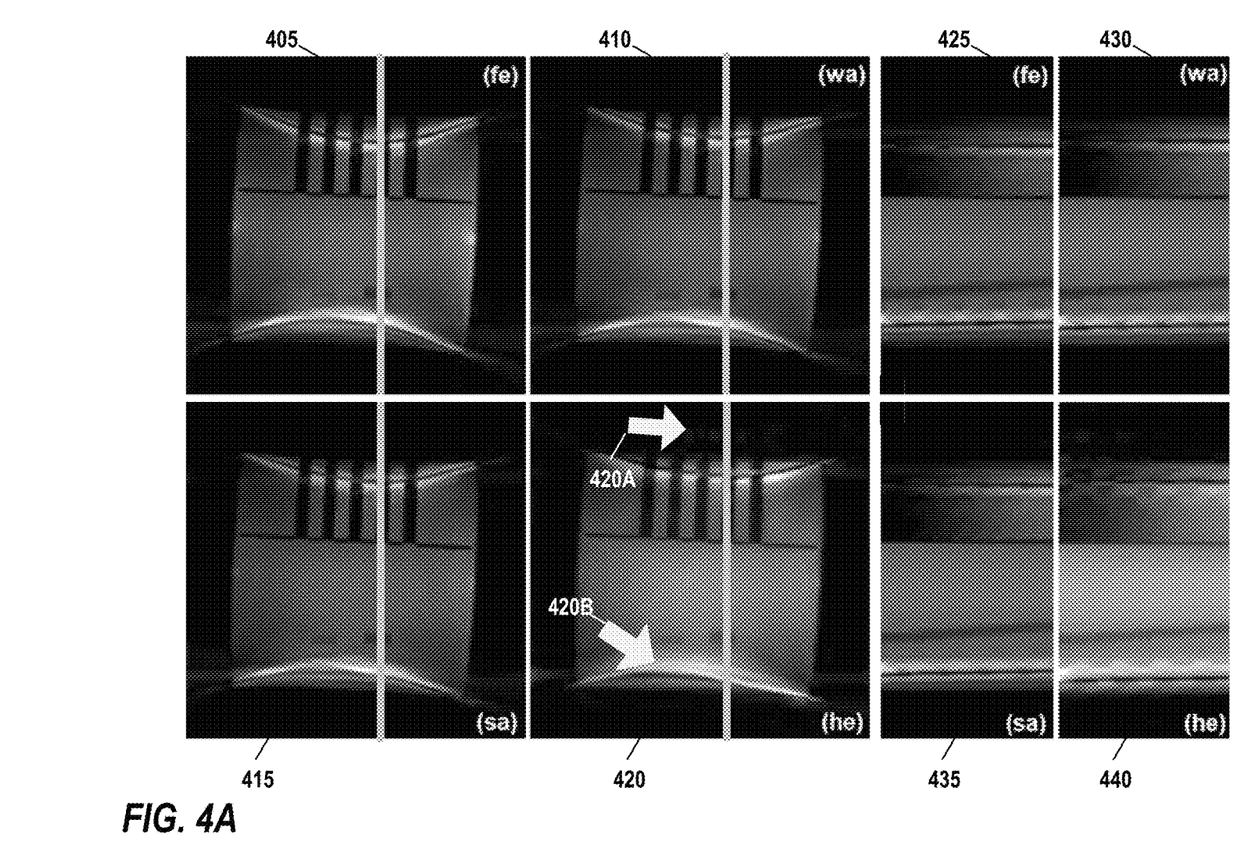
FIG. 4A provides reconstructed images and x-t plots for the phantom data, as may be generated using the techniques described herein.

FIG. 4A provides reconstructed images and x-t plots for the phantom data, as may be generated using the techniques described herein. Images 405, 410, and 415 correspond to reconstructed images full-echo, weak-asymmetric, strong-asymmetric asymmetries, respectively. Note that these three images 405, 410, and 415 show qualitatively comparable image quality. Similarly, the x-t plots in images 425, 430, and 435 illustrate qualitatively comparable temporal dynamics for full-echo, weak-asymmetric, strong-asymmetric asymmetries, respectively. However, images 420 and 440 demonstrate a noticeable degradation in quality (i.e., increased blurring and streaks, arising from bright bands around bSSFP stop bands where the slowly varying phase condition is violated) when using the half-echo k-space data. This is highlighted in image 420 with arrows 420A and 420B. These findings demonstrate that, for this particular configuration, radial CS imaging with echo asymmetries of about 50% is feasible.

Figure 4B:
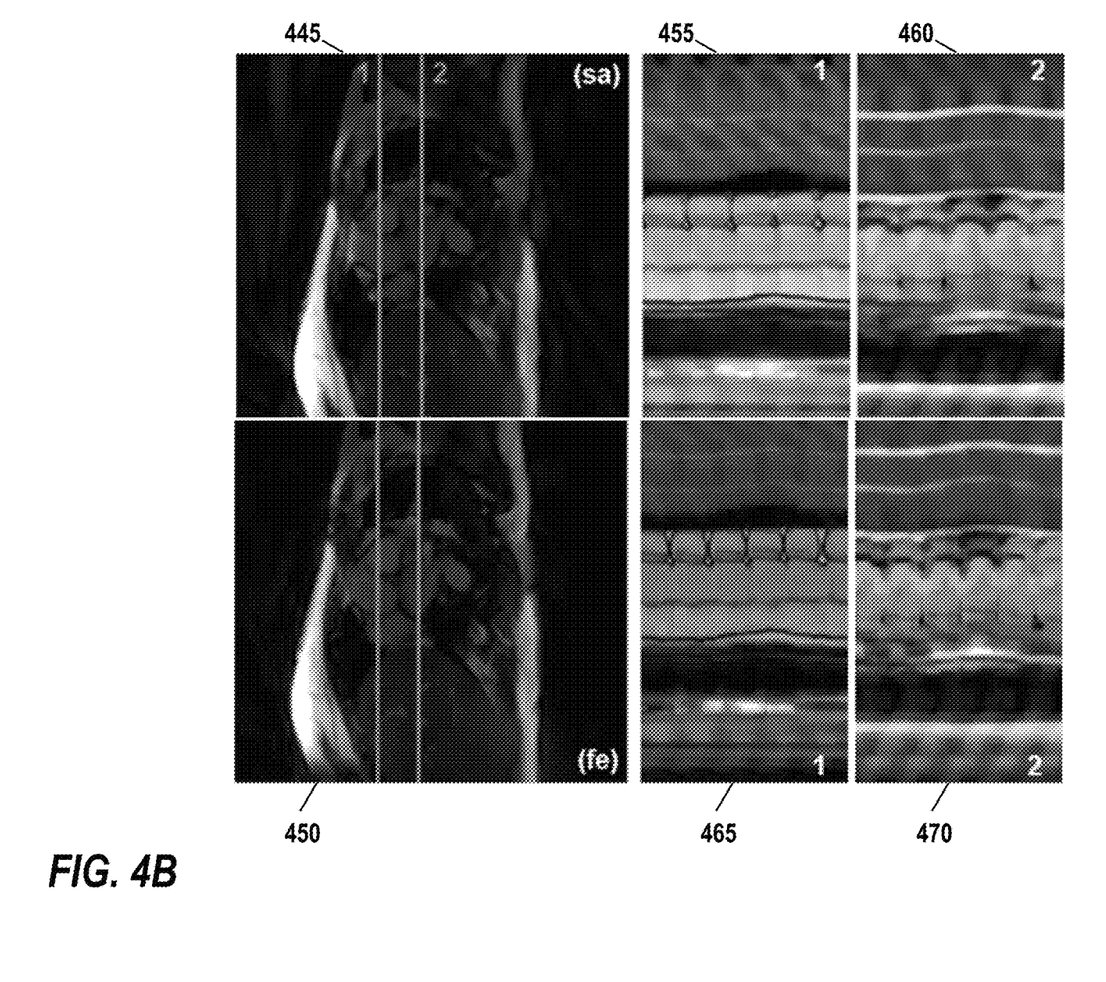
FIG. 4B provides reconstructed images and x-t plots for the cardiac data, as may be generated using the techniques described herein.

FIG. 4B provides reconstructed images and x-t plots for the cardiac data, as may be generated using the techniques described herein. The image presented in FIG. 4B compare 102 time phases of the cardiac data with asymmetries strong-asymmetric (images 445, 455, and 460) and full-echo (images 450, 465, and 470). Although radial streaks in the background are slightly increased, the reconstruction from strong-asymmetric views shown in images 445, 455, and 460 offers a similar image quality and sharpness in dynamics to the full-echo views shown in images 450, 465, and 470 due to reduced TR. These results demonstrate that sampling the k-space using radial asymmetric views (assuming sampling ~45% (i.e., 88/192) of one side of the view) can accelerate the overall acquisition with a tolerable degradation in reconstruction. Overall, these experiments show that the framework described herein in various embodiments of the present invention can speed up data acquisition and stabilize bSSFP signals by reducing TR by about 12% with only minor degradation in image quality compared to the conventional full echo schemes.

Although the embodiments discussed above describe application asymmetric radial sampling schemes with the example of bSSFP and interleaved angled sampling, it should be noted that the techniques discussed herein are generally applicable to generic MRI pulse sequences and generic sampling schemes. For example, in different embodiments, pulse sequences such as spin-echo (SE), gradient echo (GRE), or turbo-spin echo (TSE) may be used in the place of bSSFP. Similarly, in different embodiments, other sampling schemes that produce complementary patterns over successive images, such that averaging over the images generates complete k-space coverage, may be used rather than interleaved angle sampling. For example, in one embodiment, golden angle sampling is used.

Figure 5:
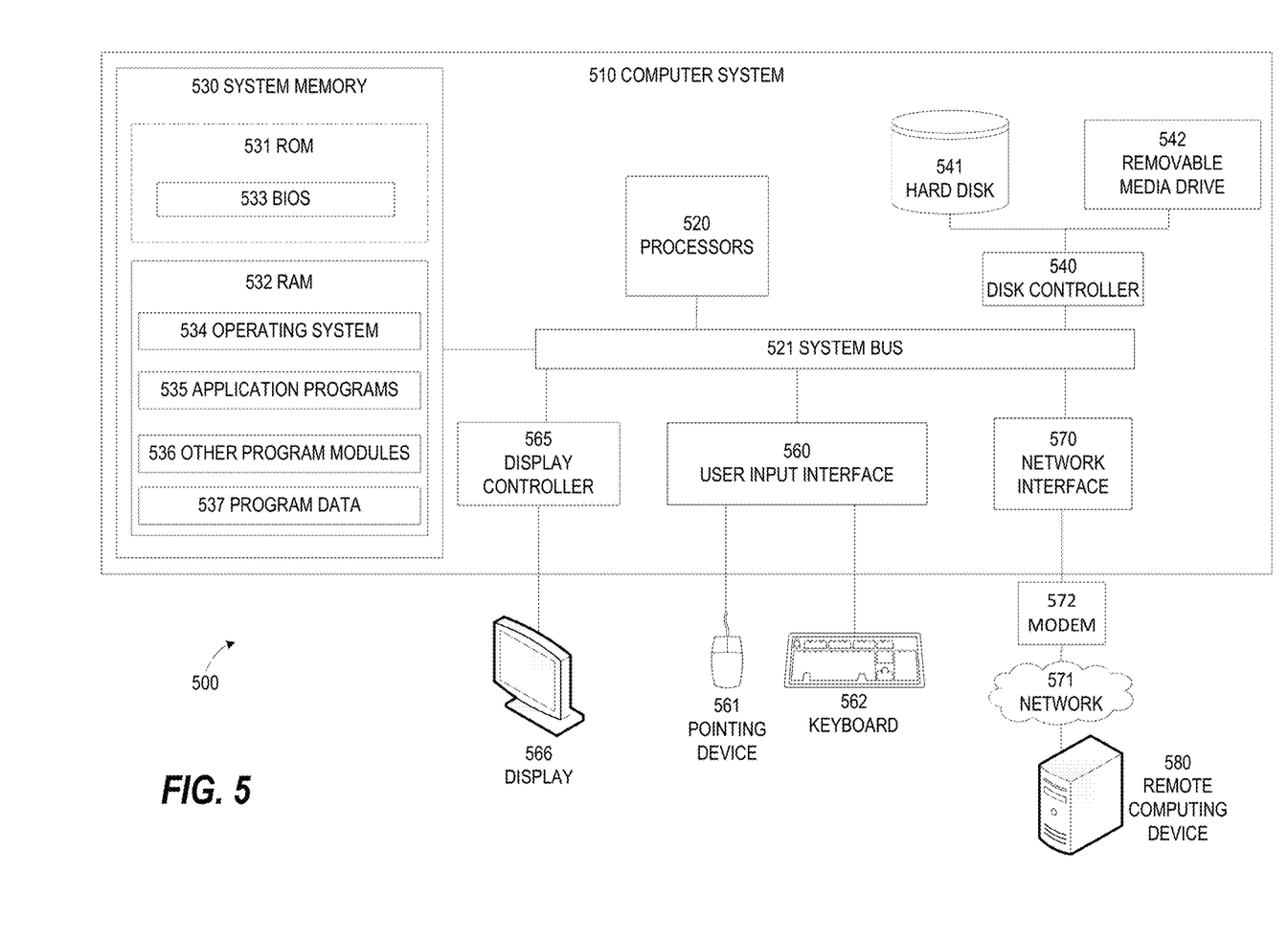
FIG. 5 illustrates an exemplary computing environment within which embodiments of the invention may be implemented.

FIG. 5 illustrates an exemplary computing environment 500 within which embodiments of the invention may be implemented. For example, this computing environment 500 may be used to implement the process 300 of determining a sampling strategy described in FIG. 3. In some embodiments, the computing environment 500 may be used to implement one or more of the components illustrated in the system 100 of FIG. 1. The computing environment 500 may include computer system 510, which is one example of a computing system upon which embodiments of the invention may be implemented. Computers and computing environments, such as computer system 510 and computing environment 500, are known to those of skill in the art and thus are described briefly here.

As shown in FIG. 5, the computer system 510 may include a communication mechanism such as a bus 521 or other communication mechanism for communicating information within the computer system 510. The computer system 510 further includes one or more processors 520 coupled with the bus 521 for processing the information. The processors 520 may include one or more central processing units (CPUs), graphical processing units (GPUs), or any other processor known in the art.

The computer system 510 also includes a system memory 530 coupled to the bus 521 for storing information and instructions to be executed by processors 520. The system memory 530 may include computer readable storage media in the form of volatile and/or nonvolatile memory, such as read only memory (ROM) 531 and/or random access memory (RAM) 532. The system memory RAM 532 may include other dynamic storage device(s) (e.g., dynamic RAM, static RAM, and synchronous DRAM). The system memory ROM 531 may include other static storage device(s) (e.g., programmable ROM, erasable PROM, and electrically erasable PROM). In addition, the system memory 530 may be used for storing temporary variables or other intermediate information during the execution of instructions by the processors 520. A basic input/output system 533 (BIOS) containing the basic routines that help to transfer information between elements within computer system 510, such as during start-up, may be stored in ROM 531. RAM 532 may contain data and/or program modules that are immediately accessible to and/or presently being operated on by the processors 520. System memory 530 may additionally include, for example, operating system 534, application programs 535, other program modules 536 and program data 537.

The computer system 510 also includes a disk controller 540 coupled to the bus 521 to control one or more storage devices for storing information and instructions, such as a hard disk 541 and a removable media drive 542 (e.g., floppy disk drive, compact disc drive, tape drive, and/or solid state drive). The storage devices may be added to the computer system 510 using an appropriate device interface (e.g., a small computer system interface (SCSI), integrated device electronics (IDE), Universal Serial Bus (USB), or FireWire).

The computer system 510 may also include a display controller 565 coupled to the bus 521 to control a display 566, such as a cathode ray tube (CRT) or liquid crystal display (LCD), for displaying information to a computer user. The computer system includes an input interface 560 and one or more input devices, such as a keyboard 562 and a pointing device 561, for interacting with a computer user and providing information to the processor 520. The pointing device 561, for example, may be a mouse, a trackball, or a pointing stick for communicating direction information and command selections to the processor 520 and for controlling cursor movement on the display 566. The display 566 may provide a touch screen interface which allows input to supplement or replace the communication of direction information and command selections by the pointing device 561.

The computer system 510 may perform a portion or all of the processing steps of embodiments of the invention in response to the processors 520 executing one or more sequences of one or more instructions contained in a memory, such as the system memory 530. Such instructions may be read into the system memory 530 from another computer readable medium, such as a hard disk 541 or a removable media drive 542. The hard disk 541 may contain one or more datastores and data files used by embodiments of the present invention. Datastore contents and data files may be encrypted to improve security. The processors 520 may also be employed in a multi-processing arrangement to execute the one or more sequences of instructions contained in system memory 530. In alternative embodiments, hard-wired circuitry may be used in place of or in combination with software instructions. Thus, embodiments are not limited to any specific combination of hardware circuitry and software.

As stated above, the computer system 510 may include at least one computer readable medium or memory for holding instructions programmed according embodiments of the invention and for containing data structures, tables, records, or other data described herein. The term "computer readable medium" as used herein refers to any medium that participates in providing instructions to the processor 520 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 541 or removable media drive 542. Non-limiting examples of volatile media include dynamic memory, such as system memory 530. Non-limiting examples of transmission media include coaxial cables, copper wire, and fiber optics, including the wires that make up the bus 521. Transmission media may also take the form of acoustic or light waves, such as those generated during radio wave and infrared data communications.

The computing environment 500 may further include the computer system 510 operating in a networked environment using logical connections to one or more remote computers, such as remote computer 580. Remote computer 580 may be a personal computer (laptop or desktop), a mobile device, a server, a router, a network PC, a peer device or other common network node, and typically includes many or all of the elements described above relative to computer system 510. When used in a networking environment, computer system 510 may include modem 572 for establishing communications over a network 571, such as the Internet. Modem 572 may be connected to bus 521 via user network interface 570, or via another appropriate mechanism.

Network 571 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 510 and other computers (e.g., remote computer 580). The network 571 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 571.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A method for acquiring cine images using a magnetic resonance imaging (MRI) system, the method comprising:
    selecting an asymmetric radial sampling scheme comprising a plurality of views at different levels of asymmetry providing an asymmetric view of k-space corresponding to a desired image resolution;
    acquiring radial k-space data using the asymmetric radial sampling scheme, wherein slice-orientation of the radial k-space data is continuously modified while acquiring the radial k-space data; and
    reconstructing a plurality of cine images from the radial k-space data using a compressed-sensing method, wherein the compressed-sensing method enforces $L_2$-type data consistency and a $L_1$-type non-smooth penalty with respect to the radial k-space data.

2. The method of claim 1, wherein the asymmetric radial sampling scheme is an interleaved-angle asymmetric radial sampling scheme.

3. The method of claim 2, wherein the interleaved-angle asymmetric radial sampling scheme comprises:
    a full-echo sampling scheme portion to be applied in a center region of k-space; and
    a secondary sampling scheme portion to be applied in a remaining area of k-space which excludes the center region of k-space.

4. The method of claim 2, wherein the interleaved-angle asymmetric radial sampling scheme is a half-echo sampling scheme.

5. The method of claim 2, wherein the interleaved-angle asymmetric radial sampling scheme distributes the asymmetric view of k-space over 2n.

6. The method of claim 1, further comprising:
    determining a density compensation value corresponding to the asymmetric view of k-space,
    wherein the compressed-sensing method applies the density compensation value during the reconstruction of the plurality of cine images.

7. The method of claim 6, wherein the density compensation value corresponding to the asymmetric view of k-space corresponds to a number of samples to be acquired in the asymmetric view of k-space.

8. The method of claim 1, wherein the compressed-sensing method incorporates an estimated coil sensitivity map generated in parallel with the reconstruction.

9. A method for acquiring cine images using a magnetic resonance imaging (MRI) system, the method comprising:
selecting an interleaved-angle asymmetric radial sampling scheme comprising a plurality of views at different levels of asymmetry providing an asymmetric view of k-space corresponding to a desired image resolution;
acquiring radial k-space data over a number of interleaves using the interleaved-angle asymmetric radial sampling scheme;
segmenting the radial k-space data into a plurality of overlapping temporal windows based on the number of interleaves; and
reconstructing iteratively a plurality of cine images from the plurality of overlapping temporal windows using a compressed-sensing method, wherein the compressed-sensing method enforces L2-type data consistency and a L1-type non-smooth penalty with respect to the radial k-space data.

10. The method of claim 9, wherein the radial k-space data is acquired using a Balanced Steady-State Free Precession (bSSFP) sequence.

11. The method of claim 9, further comprising:
determining a density compensation value corresponding to the asymmetric view of k-space,
wherein the compressed-sensing method applies the density compensation value during the reconstruction of the plurality of cine images.

12. The method of claim 11, wherein the density compensation value corresponding to the asymmetric view of k-space corresponds to a number of samples to be acquired in the asymmetric view of k-space.

13. The method of claim 9, wherein the compressed-sensing method incorporates an estimated coil sensitivity map.

14. The method of claim 13, wherein the method further comprises:
generating the estimated coil sensitivity map in parallel with the reconstruction.

15. A system for acquiring cine images using a magnetic resonance imaging (MRI) system, the system comprising:
an operator interface configured to select an asymmetric radial sampling scheme comprising a plurality of views at different levels of asymmetry providing an asymmetric view of k-space corresponding to a desired image resolution;
a plurality of radio frequency coils configured to acquire radial k-space data using the asymmetric radial sampling scheme, wherein slice-orientation of the radial k-space data is continuously modified while acquiring the radial k-space data; and
a central control computer unit configured to reconstruct a plurality of cine images from the radial k-space data using a compressed-sensing method, wherein the compressed-sensing method enforces L2-type data consistency and a L1-type non-smooth penalty with respect to the radial k-space data.

16. The system of claim 15, further comprising:
an ECG acquisition system configured to acquire a cardiac timing signal,
wherein the central control computer unit is further configured to divide the radial k-space data in a plurality of overlapping temporal windows based on the cardiac timing signal and reconstruction of the plurality of cine images is based on the plurality of overlapping temporal windows.

* * * * *